United States Patent

Hamminga et al.

[11] Patent Number: 5,037,844
[45] Date of Patent: Aug. 6, 1991

[54] SUBSTITUTED 1H-INDAZOLE-3-CARBOXAMIDES

[75] Inventors: Derk Hamminga; Ineke van Wijngaarden, both of Weesp, Netherlands

[73] Assignee: Duphar International Research B.V., Weesp, Netherlands

[21] Appl. No.: 554,918

[22] Filed: Jul. 20, 1990

[30] Foreign Application Priority Data

Jul. 25, 1989 [NL] Netherlands .................. 8901917

[51] Int. Cl.$^5$ .................. A61K 31/415; C07D 487/00
[52] U.S. Cl. .................. 514/394; 548/327
[58] Field of Search .................. 548/327; 514/394

Primary Examiner—Mary C. Lee
Assistant Examiner—Joseph K. McKane
Attorney, Agent, or Firm—Stevens, Davis, Miller & Mosher

[57] ABSTRACT

The present invention is concerned with compounds of formula 1:

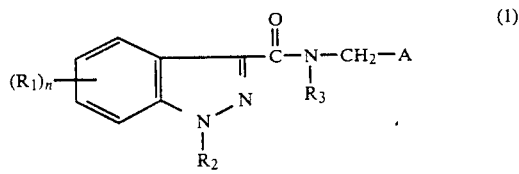

wherein
$R_1$ is straight or branched alkyl having 1-4 C-atoms, halogen or cyano;
n has the value 0-1;
$R_2$ is hydrogen, (1-6 C)alkyl, (3-6 C)alkenyl, (3-6 C)alkenyl, (3-6 C)cycloalkyl, (3-6 C)cycloalkyl-(1-4 C) alkyl, phenyl, phenyl-(1-3 C)alkyl, $COOR_6$, $COR_6$, $CONR_6R_7$ or $SO_2-R_6$, wherein $R_6$ and $R_7$ independently of each other are hydrogen, (1-6 C)alkyl, (3-6 C)cycloalkyl, phenyl or phenyl-(1-4 C)alkyl, wherein the benzene ring is optionally substituted with a methyl group or a halogen atom, with the proviso that $R_6$ is not hydrogen when $R_2$ is a group $COOR_6$ or $SO_2R_6$;
$R_3$ is hydrogen, straight or branched (1-6 C)alkyl or a phenyl-(1-3 C)alkyl group optionally substituted in the benzene ring; and
A is a group of formula 2 or 3

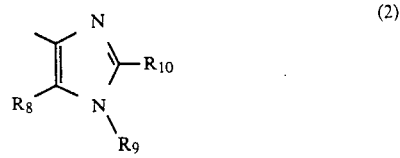

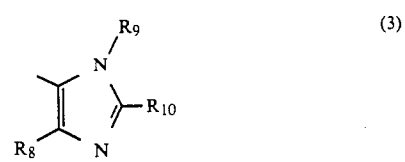

wherein one of the groups $R_8$, $R_9$ and $R_{10}$ is hydrogen, (1-C)alkyl, (3-6 C)cycloalkyl, (3-4 C)alkenyl or (3-4 C)alkynyl and the two other groups, independently of each other, are hydrogen or (1-4 C)alkyl, and the pharmacologically acceptable acid addition salts thereof, which are pharmaceutically useful as strong and selective antagonists of "neuronal" 5-hydroxy tryptamine (5-HT) receptors.

3 Claims, No Drawings

SUBSTITUTED 1H-INDAZOLE-3-CARBOXAMIDES

The invention relates to new 1H-indazole-3-carboxamides in which the amide-nitrogen atom is substituted with an imidazolyl methyl group.

It is known, inter alia from European Patent Application 86302964.1 (publication no. 0.200.444) that certain indazole carboxylic acid derivatives are 5HT-antagonists which may be used for the treatment of serotonin-induced syndromes.

It has been found surprisingly that the new compounds of formula I

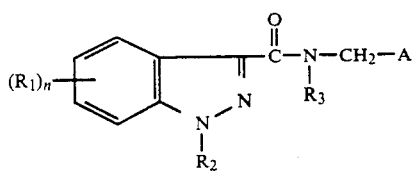

wherein
$R_1$ is halogen, cyano or straight or branched alkyl having 1–4 C-atoms;
n has the value 0–1;
$R_2$ is hydrogen, (1–6 C)alkyl, (3–6 C)alkenyl, (3–6 C)alkynyl, (3–6 C)cycloalkyl, (3–6 C)cycloalkyl-(1–4 C)alkyl, phenyl, phenyl-(1–3 C)alkyl, $COOR_6$, $COR_6$, $CONR_6R_7$ or $SO_2$—$R_6$, wherein $R_6$ and $R_7$ independently of each other are hydrogen, (1–6 C)alkyl, (3–6 C)cycloalkyl, phenyl or phenyl-(1–4 C)alkyl, wherein the benzene ring is optionally substituted with a methyl group or a halogen atom, with the proviso that $R_6$ is not hydrogen when $R_2$ is a group $COOR_6$ or $SO_2R_6$;
$R_3$ is hydrogen, straight or branched (1–6 C)alkyl or a phenyl-(1–3 C)alkyl group optionally substituted in the benzene ring; and
A is a group of formula 2 or 3

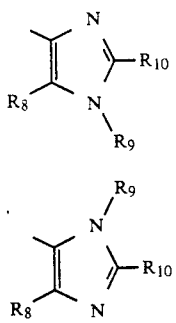

wherein one of the groups $R_8$, $R_9$ and $R_{10}$ is hydrogen (1–4 C)alkyl, (3–6 C)cycloalkyl, (3–4 C)alkenyl or (3–4 C)alkynyl and both other groups, independently of each other, are hydrogen or (1–4 C)alkyl, and the pharmacologically acceptable acid addition salts thereof are very strong and selective antagonists of "neuronal" 5-hydroxytryptamine (5-HT) receptors.

Preferred embodiments of the invention are the compounds of formula (1) wherein $R_3$ is a (1–6 C)alkyl group.

Preferred embodiments of the invention are also the compounds of formula (1) wherein the groups $R_8$, $R_9$ and $R_{10}$ have the meanings: hydrogen or (1–4 C)alkyl.

Suitable acids with which the compounds of formula I according to the invention can form pharmaceutically acceptable acid addition salts are, for example, hydrochloric acid, sulphuric acid, phosphoric acid, nitric acid, and organic acids, for example citric acid, fumaric acid, maleic acid, tartaric acid, acetic acid, benzoic acid, p-toluene sulphonic acid, methane sulphonic acid and the like.

The racemates as well as (geometric) isomers and the individual enantiomers of compounds of formula 1 belong to the invention.

The antagonistic activity of the compounds of formula 1 on the response induced by 5-HT or 2-methyl-5-HT was determined and measured in the Bezold-Jarish reflex test in rats. The affinity to "neuronal" 5-HT-receptors was determined and measured by the displacement of ($^3$H)GR 38032F from neuroblastoma cells.

On the basis of the antagonistic effect on this type of 5-HT-receptors, the compounds may be used for the treatment of symptoms which are caused by overexcitation of the said receptors a) in the gastrointestinal system (nausea and vomiting as a result of exogenic factors, for example, cancer therapy, or endogenic factors, for example, stasis of the stomach and migraine), ulcer, dyspepsia, spasms, irritable bowel syndrome, etc., or b) in the central nervous system (hallucinations, delusions, manias, depressions, anxiety, pain, nausea, improvement of vigility, etc., or c) in the cardiovascular system, for example, spasms of the vessels, arrhythmia, etc., or d) in the respiratory system (including nasal disturbances and disturbances of bronchi and lungs, or e) for relieving or preventing withdrawal symptoms which are induced by drug abuse.

The compounds according to the invention and their salts may be brought into forms suitable for administration, for example, pills, tablets, coated tablets, capsules, powders, injection liquids and the like, by means of the techniques conventionally used for this purpose and while using suitable auxiliary substances, for example, solid or liquid carrier materials.

The dosage in which the compounds according to the invention may be used depend on the severity and the nature of the disease to be treated and on the way of administration. As a rule, the dosage will be between 0.05 and 20 mg, preferably between 0.1 and 10 mg of active substance daily.

The compounds according to the invention may be prepared in a manner known per se for analogous compounds, for example:

a) by reaction of a compound of formula 4

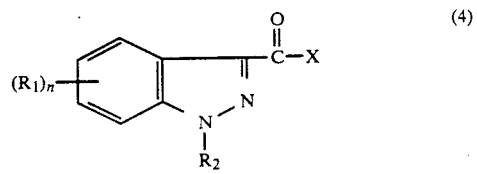

wherein $R_1$, $R_2$ and n have the meanings given in formula 1 and wherein X is a group which may be replaced by a nucleophile, for example, a halogen atom, with a compound of formula 5

wherein $R_3$ and A have the meanings given in formula 1, or wherein A is a group which after splitting off a protecting group provides a group A which has the meaning mentioned in formula 1.

The reaction is preferably carried out in a suitable solvent, for example, acetonitrile, dimethyl formamide, methylene chloride, etc., in the presence of a base, for example, triethylamine, pyridine, etc., at temperatures between 0° and 100° C.

The compounds of formula 6

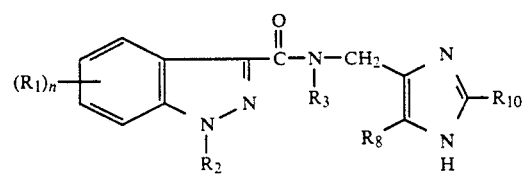

wherein $R_1$, $R_2$, $R_3$, $R_8$, $R_{10}$, and n have the meanings mentioned in formula 1, can be obtained in particular in good yield by reaction of a compound of formula 4 with a compound of formula 7 or 8

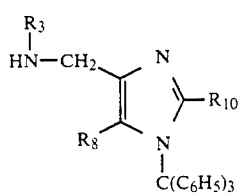

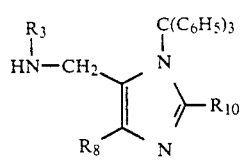

and then removing the trityl group form the resulting reaction product, for example, in acid conditions or with palladium on carbon and ammonium formiate, preferably in a suitable solvent; or b) by reaction of a compound of formula 9

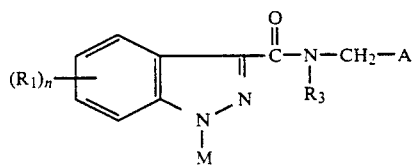

wherein $R_1$, $R_3$, n and A have the meanings mentioned in formula 1 (with the proviso that $R_9$ in group A is not a hydrogen atom) and M is an alkali metal atom, with a compound of the formula $R_2$—X, wherein $R_2$ has the meaning mentioned in formula 1 and X is a group which may be replaced by a nucleophile, for example, an iodine atom. The reaction is preferably carried out in a solvent, for example, acetonitrile, dimethyl formamide, etc., at temperatures between 0° and 150° C.; or c) by reaction of a compound of formula 10 or 11

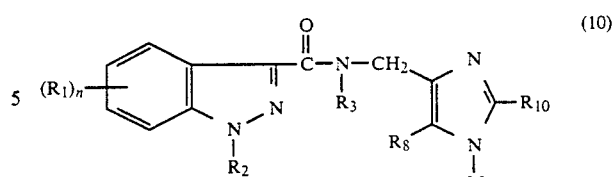

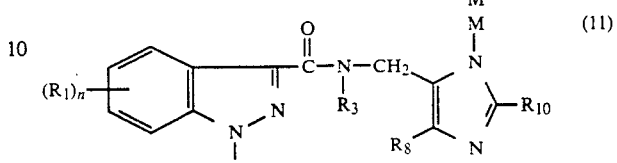

wherein $R_1$, $R_2$, $R_3$, $R_8$, $R_{10}$, and n have the meanings mentioned in formula 1 and M is an alkali metal atom with a compound of the formula $R_9$—X, wherein $R_9$ has the meaning mentioned in formula 1 and X is a group which may be replaced by a nucleophile, for example, a halogen atom.

The invention will be described in greater detail with reference to the following specific examples.

EXAMPLE

N-methyl-N-[(4-methyl-1H-imidazol-5-yl)methyl]-1 methyl-1H-indazole-3-carboxamide hydrochloride 1.4 g (7.96 mmol) of 1-methyl-1H-indazole-3-carboxylic acid were dissolved in 50 ml of chloroform. 1.7 ml (24 mmol) of thionyl chloride were added and the mixture was boiled for 1 hour. It was then evaporated in vacuo. Chloroform was added and the mixture was again evaporated in vacuo. The residue was dissolved in 40 ml of methylene chloride, after which 1.2 ml (8.7 mmol) of triethyl amine and 2.92 g (7.96 mmol) of the mixture of N-methyl-N-[(4-methyl-1-triphenylmethyl-1H-imidazol-5-yl)methyl]-amine and N-methyl-N-[(5-methyl-1-triphenylmethyl-1H-imidazol-4-yl)methyl]-amine in 20 ml of methylene chloride were added. The mixture was stirred at room temperature for 30 minutes. The reaction mixture was then shaken with water. The methylene chloride solution was washed with water, dried and evaporated in vacuo. The residue was chromatographed over silica gel using methylene chloride/ethanol (95/5) as an eluent. 2.1 g of the isomer mixture of N-methyl-N-[(4(or 5)-methyl-1 triphenylmethyl-1H-imidazol-5 (or 4)-yl)methyl]-1-methyl-1H-indazole-3-carboxamide were obtained.

The isomer mixture thus obtained (2.1 g) was brought in a mixture of 50 ml of acetic acid and 50 ml of water and boiled for 1 hour. The mixture was then evaporated in vacuo. The residue was shaken with 2N sodium hydroxide solution and with methylene chloride. The methylene chloride layer was separated and evaporated in vacuo, after which the residue was chromatographed over silica gel using methylene chloride/methanol/ammonia (92/7.5/0.5) as an eluent. The good fractions were evaporated. The residue was dissolved in ethyl acetate and alcoholic hydrochloric acid was then added. After sucking off the solid, 1.0 g of the desired hydrochloride was obtained having a melting point of 193°–194° C. $^{13}$C NMR(CDCl$_3$, Ref.: TMS, Additive: Triethyl amine):

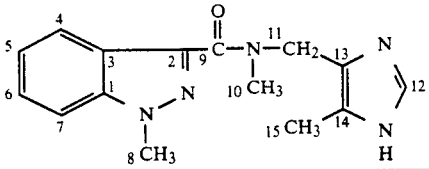

| 1 | 140.50 | S   | 6  | 127.22 | D # | 11 | 45.31  | T |
|---|--------|-----|----|--------|-----|----|--------|---|
| 2 | 138.08 | S   | 7  | 109.14 | D   | 12 | 133.87 | D |
| 3 | 124.13 | S   | 8  | 36.77  | Q   | 13 | 130.64 | S |
| 4 | 122.47 | D # | 9  | 164.35 | S   | 14 | 126.90 | S |
| 5 | 122.23 | D # | 10 | 36.01  | Q   | 15 | 10.82  | Q |
| 1 | 140.31 | S   | 6  | 126.77 | D # | 11 | 42.70  | T |
| 2 | 137.96 | S   | 7  | 109.14 | D   | 12 | 133.39 | D |
| 3 | 124.10 | S   | 8  | 36.01  | Q   | 13 | 129.28 | S |
| 4 | 122.29 | D # | 9  | 163.58 | S   | 14 | 125.35 | S |
| 5 | 122.12 | D # | 10 | 32.94  | Q   | 15 | 10.62  | Q |

Mixture of 2 amide isomers; Chemical shifts are exchangeable. Some lines are broad.

In a analogous manner were obtained:
1. N-methyl-N-{(4-methyl-1H-imidazol-5-yl)methyl}-1-allyl-1H-indazole-3-carboxamide; melting point 142°–143° C.

$^{13}$C NMR (CDCl$_3$, Ref.: TMS):

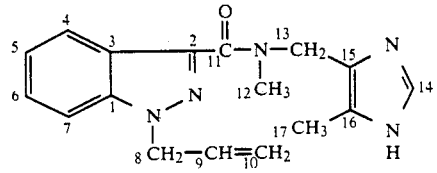

| 1 | 139.85 | S   | 7  | 109.34 | D | 13 | 42.97  | T |
| 2 | 138.43 | S   | 8  | 51.84  | T | 14 | 133.57 | D |
| 3 | 124.28 | S   | 9  | 132.18 | D | 15 | 129.00 |   |
| 4 | 122.41 | D # | 10 | 117.97 | T | 16 | 125.40 |   |
| 5 | 122.12 | D # | 11 | 163.55 | S | 17 | 10.61  | Q |
| 6 | 126.72 | D # | 12 | 32.90  | Q |    |        |   |
| 1 | 140.13 | S   | 7  | 109.34 | D | 13 | 45.39  | T |
| 2 | 138.56 | S   | 8  | 51.96  | T | 14 | 133.83 | D |
| 3 | 124.28 | S   | 9  | 132.18 | D | 15 | 130.90 |   |
| 4 | 122.52 | D # | 10 | 118.63 | T | 16 | 127.60 |   |
| 5 | 122.32 | D # | 11 | 164.15 | S | 17 | 10.92  | Q |
| 6 | 127.25 | D # | 12 | 36.65  | Q |    |        |   |

Mixture of 2 amide isomers; C.S. are exchangeable. Some lines are broad.

2. N-methyl-N-{(4-methyl-1H-imidazol-5-yl)methyl}-1-allyl-7-fluoro-1H-indazole-3-carboxamide $^{13}$C NMR (CDC$_3$, Ref.: TMS):

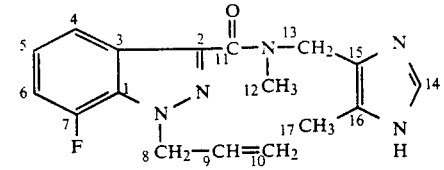

| 1 | 129.44 | S | 7  | 148.12 | S | 13 | 43.04  | T |
| 2 | 138.94 | S | 8  | 54.17  | T | 14 | 133.66 | D |
| 3 | 128.00 | S | 9  | 132.72 | D | 15 | 130.47 | S |
| 4 | 118.24 | D | 10 | 117.96 | T | 16 | 123.90 | S |
| 5 | 122.72 | D | 11 | 162.86 | S | 17 | 11.02  | Q |
| 6 | 111.51 | D | 12 | 32.95  | Q |    | *.00   |   |

COUPLING CONSTANTS:
J(7,F18) = 247.8   J(6,F18) = 17.4   J(1,F18) = 13.1
J(5,F18) = 5.8    J(4,F18) = 4.4    J(3,F18) = 3.6

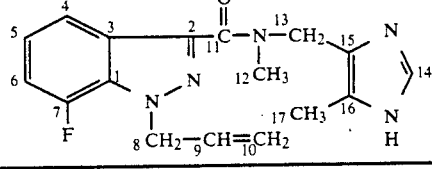

| 1 | 129.82 | S | 7  | 148.17 | S | 13 | 45.04  | T |
| 2 | 139.39 | S | 8  | 54.21  | T | 14 | 133.96 | D |
| 3 | 128.19 | S | 9  | 132.78 | D | 15 | 132.60 | S |
| 4 | 118.53 | D | 10 | 118.79 | T | 16 | 126.21 | S |
| 5 | 123.02 | D | 11 | 163.98 | S | 17 | 11.34  | Q |
| 6 | 112.14 | D | 12 | 36.98  | Q |    | *.00   |   |

COUPLING CONSTANTS:
J(7,F18) = 247.8   J(6,F18) = 17.4   J(1,F18) = 12.4
J(5,F18) = 5.1    J(4,F18) = 4.4    J(3,F18) = 2.9

Mixture of 2 amide isomers; C.S. are exchangeable. Some lines are broad.

We claim:
1. Compounds of formula 1:

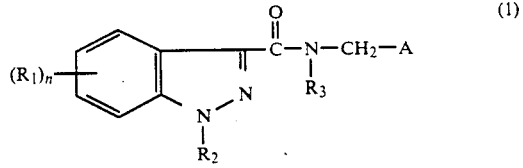

wherein
R$_1$ is straight or branched alkyl having 1–4 C-atoms, halogen or cyano;
n has the value 0–1;
R$_2$ is hydrogen, (1–6 C)alkyl, (3–6 C)alkenyl, (3–6 C)cycloalkyl, (3–6 C)cycloalkyl-(1–4 C)alkyl, phenyl, phenyl-(1–3 C)alkyl, COOR$_6$, COR$_6$, CONR$_6$R$_7$ or SO$_2$—R$_6$, wherein R$_6$ and R$_7$ independently of each other are hydrogen, (1–6 C)alkyl, (3–6 C)cycloalkyl, phenyl or phenyl-(1–4 C)alkyl, wherein the benzene ring is optionally substituted with a methyl group or a halogen atom, with the proviso that R$_6$ is not hydrogen when R$_2$ is a group COOR$_6$ or SO$_2$R$_6$;
R$_3$ is hydrogen, straight or branched (1–6 C)alkyl or a phenyl-(1–3 C)alkyl group optionally substituted in the benzene ring; and
A is a group of formula 2 or 3

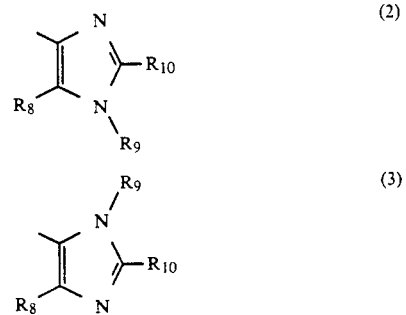

wherein one of the groups R$_8$, R$_9$ and R$_{10}$ is hydrogen, (1–4 C)alkyl, (3–6 C)cycloalkyl, (3–4 C)alkenyl or (3–4 C)alkynyl and the two other groups, independently of each other, are hydrogen or (1–4 C)alkyl, or a pharmacologically acceptable acid addition salt thereof.

2. Pharmaceutical compositions which comprise a compound as claimed in claim 1 as the active substance.

3. A method of treating syndromes caused by serotonin, by administering an effective amount of a compound as claimed in claim 1.

* * * * *